(12) United States Patent  
Huang

(10) Patent No.: US 6,355,211 B1
(45) Date of Patent: Mar. 12, 2002

(54) METHOD FOR MANUFACTURING HIGH PERFORMANCE COMPONENTS

(76) Inventor: Xiaodi Huang, 406 $2^{nd}$ St., Houghton, MI (US) 49931

( * ) Notice: Subject to any disclaimer, the term of this patent is extended or adjusted under 35 U.S.C. 154(b) by 0 days.

(21) Appl. No.: 09/497,420

(22) Filed: Feb. 7, 2000

Related U.S. Application Data

(62) Division of application No. 09/211,040, filed on Dec. 15, 1998, now Pat. No. 6,042,780.

(51) Int. Cl.$^7$ .................................................. B22F 3/14
(52) U.S. Cl. .................... 419/49; 419/7; 419/36; 419/45; 419/49; 419/54; 264/604; 264/607; 264/610
(58) Field of Search .................. 419/37, 38, 36, 419/5, 7, 49, 53, 54, 45; 264/604, 607, 610

(56) References Cited

U.S. PATENT DOCUMENTS

| | | | | |
|---|---|---|---|---|
| 4,314,399 A | * | 2/1982 | Severinsson ................. 29/420 |
| 4,584,171 A | * | 4/1986 | Niino et al. .................... 419/8 |
| 4,591,470 A | * | 5/1986 | Goto et al. ..................... 264/59 |
| 5,482,671 A | * | 1/1996 | Weber .......................... 419/36 |
| 5,503,795 A | * | 4/1996 | Hubbard ....................... 419/38 |
| 5,678,162 A | * | 10/1997 | Barlow et al. ................. 419/2 |
| 5,770,136 A | * | 6/1998 | Huang ......................... 264/101 |
| 5,926,685 A | * | 7/1999 | Krebs et al. ................... 419/2 |
| 5,976,457 A | * | 11/1999 | Amaya et al. ................ 419/36 |
| 6,022,509 A | * | 2/2000 | Matthews et al. ............ 419/38 |
| 6,042,780 A | * | 3/2000 | Huang ......................... 419/36 |

* cited by examiner

Primary Examiner—Daniel J. Jenkins
(74) Attorney, Agent, or Firm—Dykema Gossett PLLC

(57) ABSTRACT

A method for producing high performance components by the consolidation of powdered materials under conditions of hot isostatic pressure. The method uses the inclusion of reactive materials mixed into pressure-transmitting mold materials and into the powder to be consolidated to contribute to in-situ materials modification including purification, chemical transformation, and reinforcement. The method also uses encapsulation of the mold in a sealed container to retain the mold material in position, and to exclude air and contaminants.

9 Claims, 4 Drawing Sheets

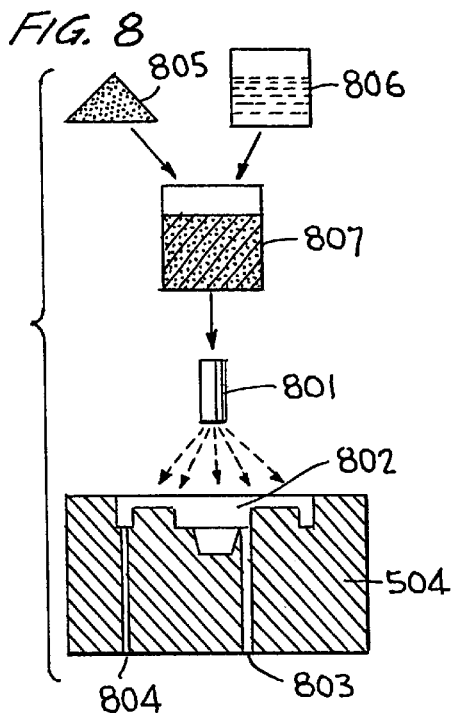
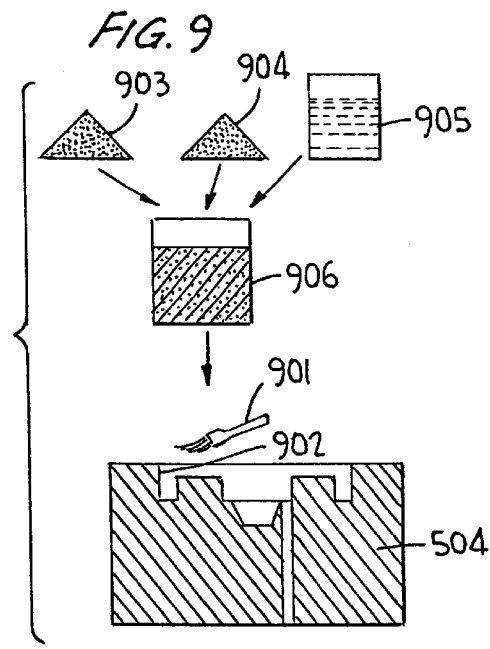
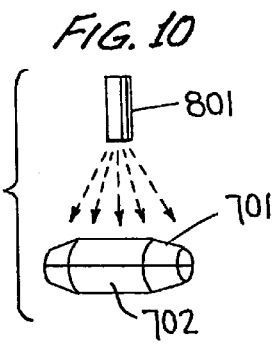
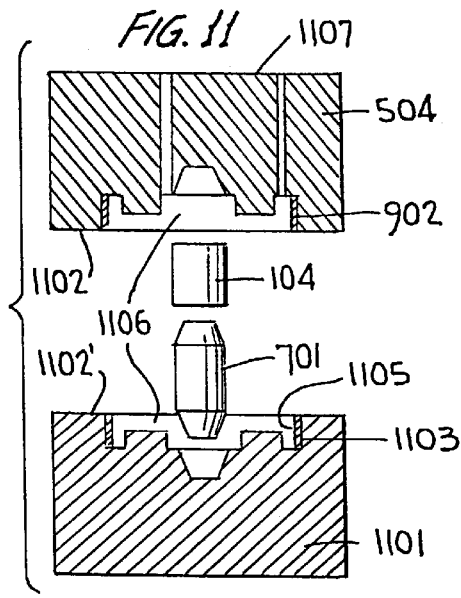
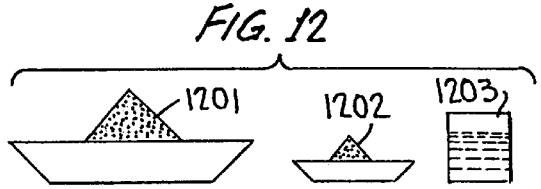
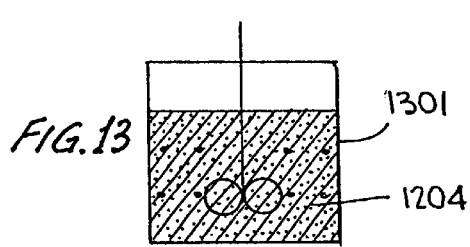
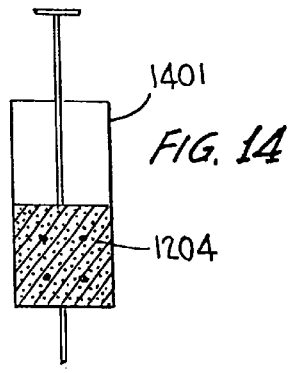

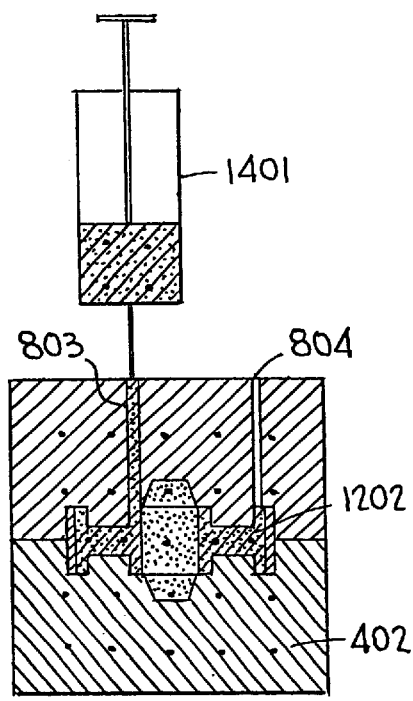
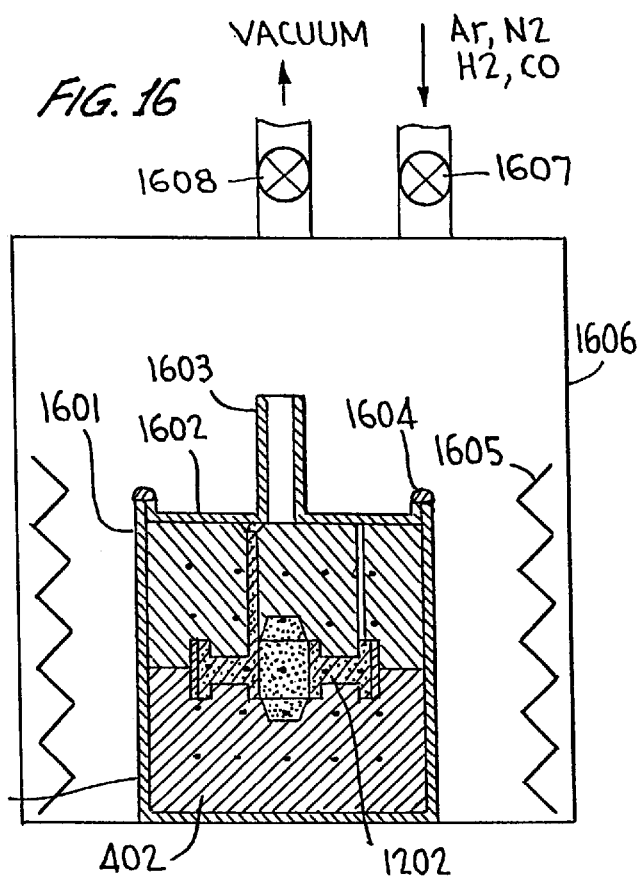
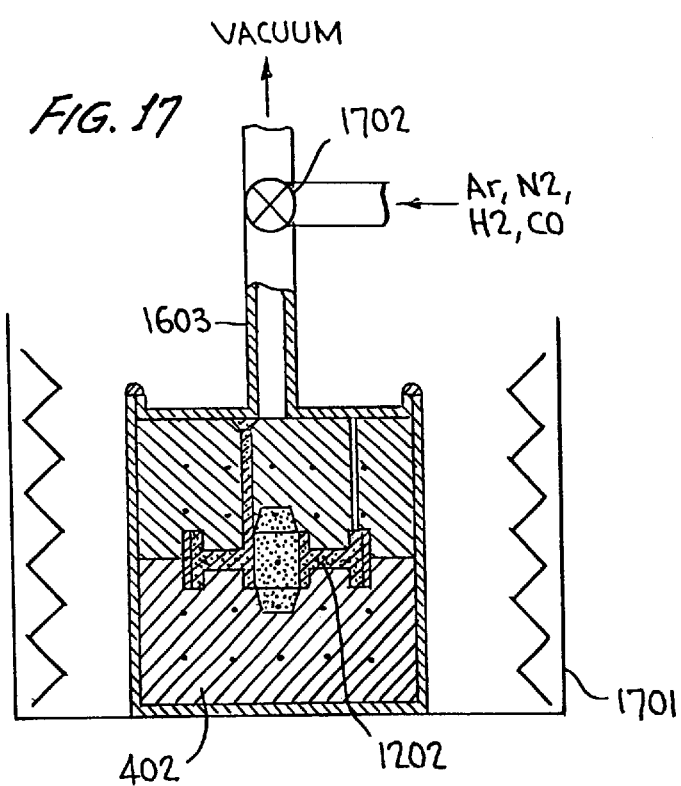
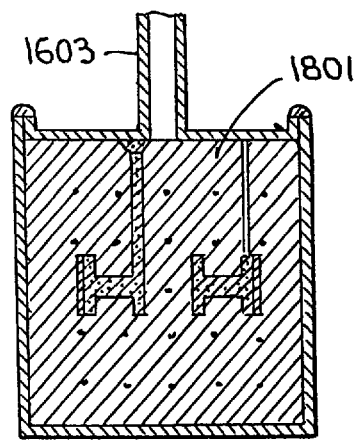

METHOD FOR MANUFACTURING HIGH PERFORMANCE COMPONENTS

CROSS REFERENCE TO RELATED APPLICATION

This application is a divisional of application Ser. No. 09/211,040, filed Dec. 15, 1998, now U.S. Pat. No. 6,042,780, the priority of which is claimed.

FIELD OF THE INVENTION

The present invention relates to a hot isostatic pressing method used for manufacturing metallic, intermetallic, ceramic, composite, hybrid, and coated articles from powdered materials. More particularly, the invention relates to a method that employs encapsulated processing, in-situ materials modification, advanced pattern-making, and surface coatings, to achieve articles with superior characteristics.

BACKGROUND OF THE INVENTION

The present invention is an improvement over the invention disclosed and claimed in U.S. Pat. No. 5,770,136, the disclosure of which is hereby incorporated by reference.

Powder consolidation technology has been associated with significant improvements in the characteristics of various materials. The results have included articles with improved manufacturability and performance for such applications as aircraft, armaments, automobiles, machinery, tooling, medical devices, and other products. Articles produced using these techniques may have complex shapes, bonded coatings, special surfaces, and may require minimal, or no, post-molding processing. Problems with the prior art include in-process materials contamination resulting in degraded performance, limited opportunities for in-situ materials modification, and high manufacturing costs. The purpose of this invention is to provide a method producing a wide variety of high performance articles, in one process, at lower cost.

SUMMARY OF THE INVENTION

In the present invention particulates are mixed with binders as pressure-transmitting molding media. According to the invention, a pattern is prepared and then a mold medium, comprising a mixture of particulate and binder, is charged over the pattern to produce, after the binder has cured, a mold with the desired cavity. A powdered material is fed into the cavity conforming to the mold's geometry. The mold serves as a pressure-transmitting medium during a consolidation process.

As an alternative, particulates are mixed with a polymer powder or a liquid polymer to form a dry mix or a wet mix. A mold is produced by beam sintering or curing the polymer, bonding the particulates into the desired shape using stereolithography (SLA).

As another alternative, particulates are mixed with a polymer powder or a liquid polymer to form a dry mix or a wet mix. A mold is produced by beam sintering or curing the polymer, bonding the particulates into the desired shape using selective laser sintering (SLS).

As yet another alternative, particulates are mixed with a polymer powder or a liquid polymer to form a dry mix or a wet mix. A mold is produced by beam sintering or curing the polymer, bonding the particulates into the desired shape using fused deposition modeling (FDM).

As yet another alternative, a mold is produced by machining blocks, made of particulate and binder, and assembling the machined blocks into a completed mold. A glue may be used to hold the blocks together.

It is an object of the invention to prevent contamination of powdered material by harmful gases released from the particulate and binder. To this end, one or more contamination eliminating materials may be included. The contamination eliminating material is selected to have an affinity for the harmful gases that, at elevated temperatures, is higher than that of the powdered material. The contamination eliminating material is added into the molding medium, or into the powdered material.

It is a further object of the invention to produce a coated article. To this end, a slurry, or a paste, or dry particles, containing the desired coating material is applied or attached to part, or all, of the surface of the cavity within the mold. Subsequently, the cavity is filled with powdered material. A high-pressure consolidation step later integrates coating and powder. The coating can be applied as single layer, or multiple layers. Each layer may be comprised of a single material or of multiple materials (phases). The coating may be solid, porous, smooth or rough. In order to produce a hybrid article, one or more inserts may be placed into the mold cavity prior to filling with powdered material.

After transferring the mold into a container, the mold is heated to an elevated temperature. The temperature profile during this initial heating phase, and the surrounding atmosphere, may be controlled for improved results. This heating cycle may serve to burn or evaporate the binder, and to eliminate contaminating gases. It may also serve to transform the powdered material partially or entirely into another material through chemical reaction. A modifying reactant may be included to participate in this chemical reaction.

The container is then covered, evacuated, and sealed. After sealing, the container is heated again and compressed isostatically at elevated temperatures to consolidate the powdered material. The mold serves as a pressure-transmitting medium. After consolidation, the material surrounding the article is removed. The article may be blasted with sand to clean its surface or etched with an acid. One phase of a coating material may be dissolved to produce a porous coating.

The present invention solves problems resulting from contamination of powdered materials by harmful gases released by particulates and binders, as well as problems encountered in lowering production cost and reducing lead time for single, and small quantity, production runs.

Diffusion bonding is a technique to bond materials together to produce specially structured articles, or to bond dissimilar materials together to produce special hybrid articles. High temperatures and pressure are required for a diffusion bonding process. This invention expands diffusion bonding to wider uses. This invention not only provides the required high temperature and pressure, but also provides the ability to bond a solid to a solid, a solid to a powder, a powder to a powder, or two or more different components at the same time. This invention also provides an easy way to bond components with various shapes and dimensions at almost any location and angle. Such bonding would otherwise be difficult, or impossible. By adding a contamination eliminating material in the mold and conducting an initial reaction heating and contamination eliminating process, the bonding surfaces of components are cleaned chemically. This results in excellent bond quality.

The major advantages of the present invention are: (1) great flexibility, (2) high product quality, (3) competitive production cost, and (4) ability to incorporate various coating and bonding steps, including in-situ porous coating and calcium phosphate material to produce medical devices.

BRIEF DESCRIPTION OF THE DRAWINGS

The present invention may be more fully understood with reference to the accompanying drawings, wherein:

FIG. 8 illustrates applying an insulation coating comprised of ceramic powder in a slurry to the internal surfaces of the partial mold with a sprayer;

FIG. 9 illustrates applying a functional coating comprising TiC and cermet powder to selected internal surfaces of a partial mold by repeated applications with a brush;

FIG. 10 illustrates the application of a coating to the external surface of a core by spraying;

FIG. 11 illustrates the assembly of the partial molds, along with a core and an insert cylinder to form a completed mold;

FIG. 12 illustrates the provision of the components of a charging mixture comprising a powder to be consolidated, a contamination eliminating material, and a carrying liquid;

FIG. 13 illustrates the mixing of the components of the charging mixture by mixing in a blender;

FIG. 14 illustrates the charging of the charging mixture into an injector;

FIG. 15 illustrates the filling of the charging mixture into the mold cavity through the sprue using the injector;

FIG. 16 illustrates the insertion of the charged mold into a container, followed by the covering and sealing of the container with a lid that includes a stem, and the initial reaction heating of the container and contents in a vacuum furnace for in-situ modification of the container's contents;

FIG. 17 illustrates an alternative embodiment wherein the sealed container is evacuated through the stem, and the furnace chamber is operated in an ambient atmosphere;

FIG. 18 illustrates the container and contents after initial reaction heating, at a point in the process where the binder has been removed from the mold material, and the geometry of the is mold and powder is maintained by the container and by inter-particle friction;

DETAILED DESCRIPTION OF THE INVENTION

Figure 1:
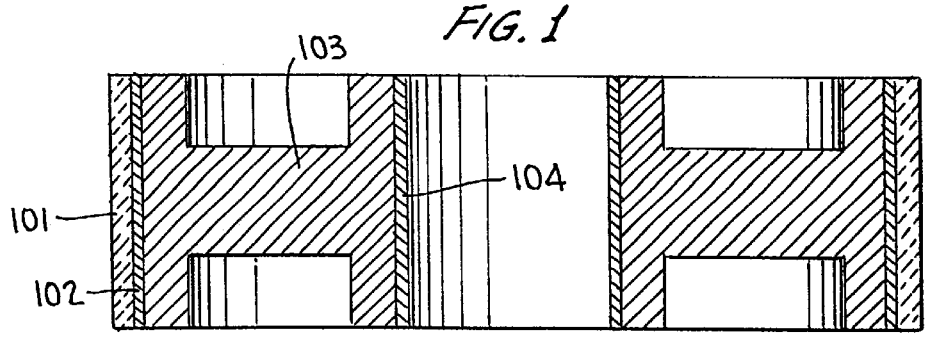
FIG. 1 illustrates a high performance wheel to be produced by using the present invention.
Figure 2:
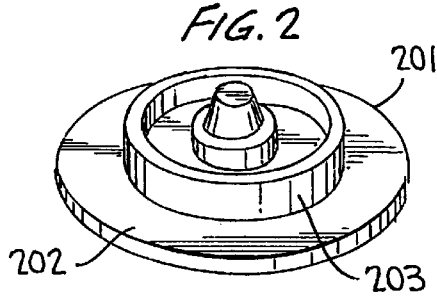
FIG. 2 illustrates a plate pattern corresponding to one half of said wheel.
Figure 3:
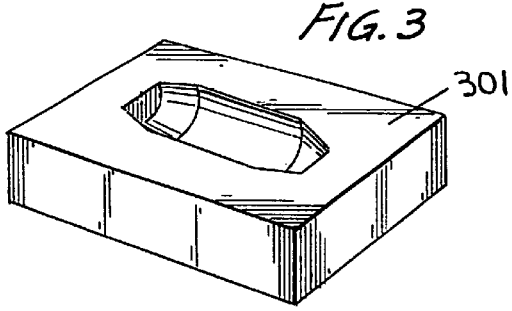
FIG. 3 illustrates a core box.
Figure 4:
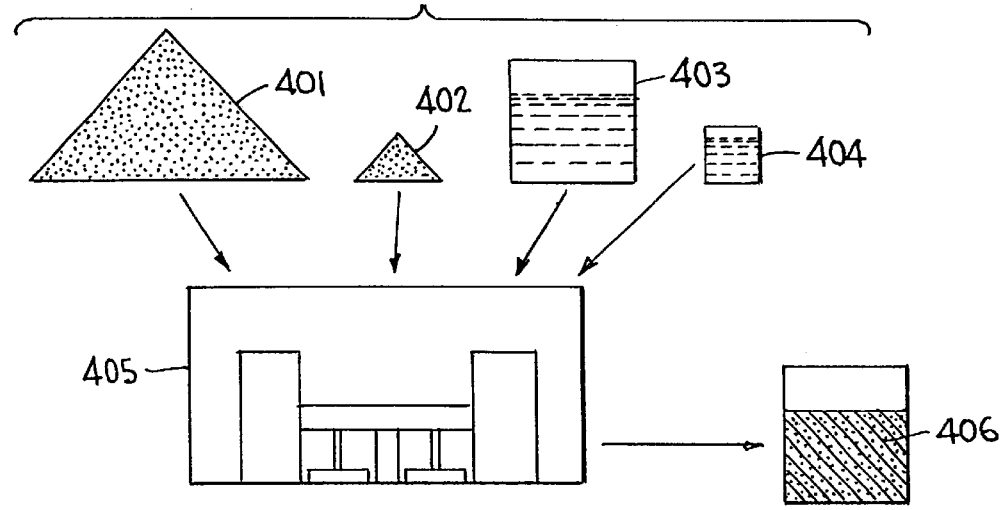
FIG. 4 illustrates mixing particulate, contamination eliminating material, binder and catalyst in a muller mixer to form a mold material.
Figure 5:
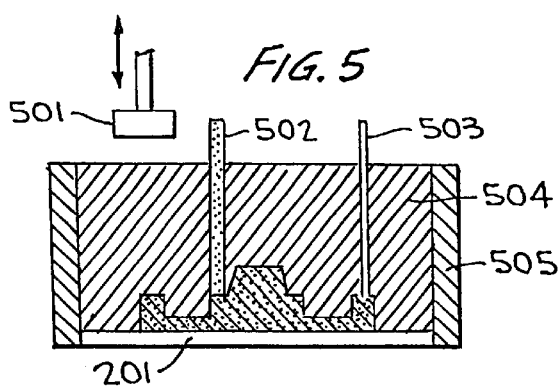
FIG. 5 illustrates forming a partial mold, here a cope, by filling and tamping mold material over a plate pattern placed in a flask.
Figure 6:
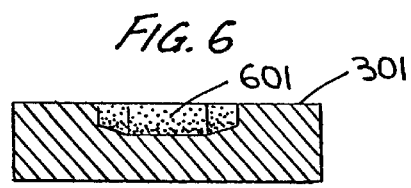
FIG. 6 illustrates filling a core box with mold material to form a half core.
Figure 7:
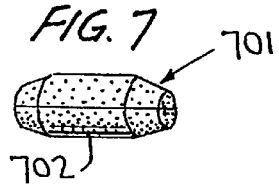
FIG. 7 illustrates assembling two half cores to form a core.

Referring to FIG. 1, a high performance wheel to be produced comprises a cermet layer 101 of 70 vol % TiC and 30 vol % cobalt alloy as a surface wear resistance material, a copper layer 102 to coordinate the property difference between the cermet layer and the body 103 of stainless steel, and a tool steel cylinder 104. FIG. 2 shows a plate pattern 201 used to make a partial mold such as a mold cope 504, or a mold drag 1101, as seen in FIG. 5 and FIG. 11 respectively. Note that the plate pattern includes a flange 202 having an outer surface 203. FIG. 3 shows a core box, 301 used for making half-cores. As seen in FIG. 4, the process begins by providing a particulate material 401 (which serves as a molding/pressure-transmitting medium), a contamination eliminating material (CEM) 402, a liquid binder 403, and a catalyst 404. The particulate material 401, CEM 402, binder 403, and catalyst 404 are introduced into a muller mixer 405, which is operated to produce a homogenous mixture referred to as the mold material 406. Referring to FIGS. 5 and 8, in order to make a mold cope 504, a plate pattern 201 is placed within a flask 505, a first removable bar 502 and a second removable bar 503 are placed within the flask 505 to form a sprue 803 and a vent hole 804 respectively. Mold material is filled into the flask, and tamped in place using a compactor 501. The mold material is allowed to cure, and the pattern 201 is stripped from the mold, exposing a first internal surface, which bounds a first partial cavity 802. To make a mold drag, a plate pattern 201 is placed in a flask without bars 502 or 503. Mold material is filled into the flask, and tamped in place using a compactor. The mold material is allowed to cure, and the pattern is stripped from the mold, exposing a second internal surface, which bounds a second partial cavity. Referring to FIG. 3, a core box 301 is provided for making a half core 601 as seen in FIG. 6. The core box is filled with mold material prepared as described above. The mold material is tamped using the compactor 501, scraped down with a tool, and allowed to cure to form a first half core. The completed half-core 601 is stripped from the core box by shaking, shocking, and the use of scraping tools. The core box is refilled, tamped, scraped and allowed to cure again to form a second half-core which is also stripped. The first and second half-core are assembled with a mixture of binder and catalyst to form a core 702, as seen in FIG. 7, with an external surface 701.

Referring to FIG. 8, an insulation coating 807 is prepared by mixing a ceramic powder 805 with a binder 806. The insulation coating is sprayed with a sprayer 801 on the internal surfaces of the partial cavity 802 of the cope 504, and on the external surface 701 of the core 702, as seen in FIG. 10.

As seen in FIG. 9, a coating mixture 906 is prepared by supplying and combining 70 vol % TiC powder 903 with 30 vol % cobalt alloy (cermet) powder 904, a binder 905. The coating mixture plied to the curved surface 902 of cope 504 as a first functional coating material by using a brush 901. After drying, the coating step is repeated many times until a thickness of coating is built up. This functional material eventually becomes layer 101 of FIG. 1, as hereinafter described. A mixture of copper powder and a binder is applied, as second functional coating material over the TiC and cobalt cermet coating, in the same way. This second functional coating eventually becomes layer 102 of FIG. 1, as hereinafter described. FIG. 11, in connection with FIG. 5, shows a drag 1101 formed in the manner discussed in relation to the cope. This drag has been processed in the same manner as shown in FIGS. 8 and 9, to form a pair of functional layers 1105 on curved surface 1103 of the drag. A binder is applied to the internal surface of a tool steel cylinder 104, the two ends of the core 702, and the parting surfaces 1102 and 1102' of the mold cope 504 and mold drag 1101 respectively. The mold cope 504, mold drag 1101, core 702, and cylinder 104 are assembled according to FIG. 11 resulting in a complete interior cavity 1106 and an external surface 1107.

Referring to FIG. 12, a powdered material 1201, a contamination eliminating material 1202, and a selected carrying liquid 1203 are provided. Note that in various embodiments the powdered material may be fed dry, and no carrying liquid is required. In the present embodiment the powdered material 1201, the contamination eliminating material 1202, and the carrying liquid 1203 are mixed in a blender 1301 as shown in FIG. 13.

The resulting charging mixture 1204 is then charged into an injector 1401, see FIG. 14. As seen in FIG. 15, the injector 1401 is used to wet fill the charging mixture 1204 into the interior cavity of the mold through sprue 803. During filling, air is vented through vent hole 804. Due to the porous nature of the cured mold material, liquid may be sucked into, or absorbed by, the surrounding mold material to concentrate the charging mixture to be consolidated, and promote drying. Referring to FIG. 16, the entire mold is then placed in a container 1601 having an external surface 1609. A cover 1602, with a stem 1603, is joined to the container 1601 by welding 1604 circumferentially around the cover. An initial reaction heating step is performed, with associated contamination elimination. The container 1601 is heated by the heater 1605 in an air tight chamber 1606, which can be evacuated through a passageway with a valve 1608, or filled with Ar, $N_2$, $H_2$, or CO under controlled pressure, though a passageway with valve 1607. During a selected heating procedure, the chamber 1606 is repeatedly evacuated and filled with one or more gases. The object of this procedure is to remove organic binders, and to release, react and fix with the contamination eliminating materials 402, undesirable gases from binders, molding media, coating materials, and the powdered material 1201.

As an alternative, as seen in FIG. 17, the step of reaction heating and contamination elimination is performed with the furnace chamber 1701 open, and a three way valve 1702 is used to facilitate the evacuation and filling of gas through the stem 1603.

Figure 19:
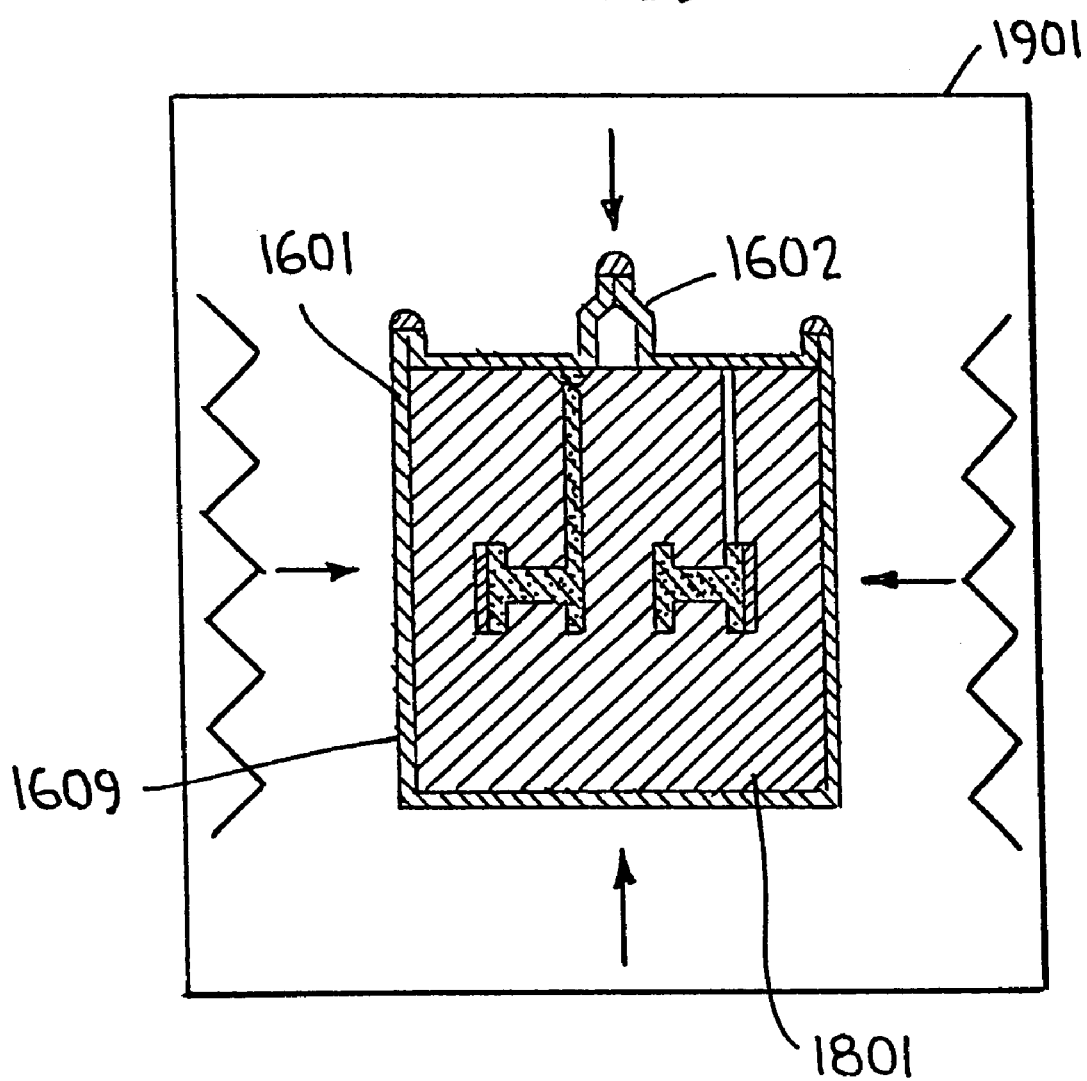
FIG. 19 illustrates the application of hot isostatic pressure to the external surface of the container, which pressure is transmitted by the particulate material to the powdered material to be consolidated, resulting in consolidation of the powder into a solid article.

Referring to FIG. 18 after the initial reaction heating the container is moved out of the furnace chamber. The organic binders have been removed, and the original cope, drag, and core have become unbonded particles 1802. Due to chemical reaction, the contamination eliminating material 1202 has become a gas and removed, or dissolved in the powdered material 1201, or formed a fine reinforcement in the powdered material 1201. Vacuum is applied to the open end of stem 1603 to remove gases from the interior of the container, whereupon the stem is crimped and welded to hermetically seal the container as seen in FIG. 19. The sealed container is subjected to a combination of elevated temperature and high isostatic pressure in a furnace chamber 1901 to compress the container 1601 and consolidate the powdered material and the functional coating materials. The consolidation pressure is applied through the walls of the container and through the pressure-transmitting molding media 1801. After consolidation is complete, the completed article is removed from the surrounding media, cutting away the container if necessary. Post treatment is then carried out according to means well known in the art.

The process is amenable to a wide variety of alternative modes of practice which bring the benefits of the invention to the manufacture of many articles of various description. These variations may be generally described in terms of the ten steps typically required, as listed below:
1. pattern making
2. preparing mixture of molding/pressure-transmitting medium and binder,
3. mold making and core making,
4. coating,
5. implanting and mold assembly,
6. powder preparation and filling,
7. initial reaction heating and contamination elimination,
8. evacuation and sealing,
9. consolidation, and
10. post treatment.

The ten steps above are not to be construed as limiting the scope of the invention. Some of the steps may not be necessary, and some additional steps may be required to manufacture particular articles. For example, two alternative methods are provided to replace steps 1 to 3 in making some articles.

Pattern Making

A pattern may be used to form the cavity of a mold made of particulate material and binder in this invention. The pattern is surrounded by a mixture of particulate material and binder which then assumes the inverse shape of the pattern after the binder is cured. The pattern is made of shapeable material such as wood, metal, plastic, paper, or composite materials.

Pattern making begins with determining the required dimensions of an article. Patterns are oversized to compensate for shrinkage or contraction of the article material during consolidation and cooling, and to compensate for any extra material to be removed from machined surfaces of the article.

In order to produce a texture or a rough surface on a finished article, such as a surgical implant, the pattern surface is engraved correspondingly.

Preparing Mixture of Molding/pressure-transmitting Medium and Binder

Ceramic, metallic, intermetallic or carbon (graphite) particulate material, or their mixtures are used as the molding/pressure-transmitting media. 0.5 percent by weight (wt %) to 20 wt % organic or inorganic binder is used to bond the particulate material. An organic binder is preferred. The binder is cured by heating, by a gas such as $CO_2$, or by use of a catalyst.

Particulate material and binders always release gases during heating. These gases cause contamination of powdered materials used to form an article, such as aluminum, copper, nickel, steel, cobalt or titanium. Oxides, nitrides, carbides, sulfides, chlorides, phosphides, and other compounds may form on the powder surfaces, resulting in articles with poor mechanical properties. Even a few parts per million (ppm) of these gases may cause a serious problem. To solve the problem, 0.001 wt % to 20 wt % of one or more contamination eliminating materials is added into the mixture of particulate material and binder. A contamination eliminating material is defined as having a higher affinity, at an elevated temperature, to a harmful gas than the powdered material used to form the article. For example, a titanium article might be made of a titanium powder using this invention. Titanium powder is very reactive with oxygen desorbed from the surfaces of the particulate material, and with the $CO_2$ and $H_2O$ released from the binder, during heating. To protect the titanium powder from oxidation, magnesium powder is added into the mixture of particulate material and binder. Magnesium is the contamination eliminating material as defined above because, at an elevated temperature, magnesium has a higher affinity for oxygen, $CO_2$, and $H_2O$ than titanium. In order to increase the reactivity, or surface area, of the contamination eliminating material for reaction with harmful gases, the contamination eliminating materials are usually used in powder form in sizes ranging from 0.01 μm to 5 mm. The contamination eliminating materials used in this invention include materials containing sodium, potassium, yttrium, lithium, beryllium, calcium, scandium, strontium, zirconium, barium, aluminum, titanium, magnesium, manganese, silicon, carbon, copper, zinc, $CaH_2$, and rare-earths.

The mold materials, including particulate material, binders, catalysts, and contamination eliminating materials are charged into mixing equipment in a designed ratio and sequence. The mixing schedule is determined by the type of device used and the particulate material and binder system selected.

$CaCO_3$ is an abundant and cheap material and it decomposes at about 900° C. in air according to the equation:

$$CaCO_3 = CaO + CO_2$$

The resultant CaO has a melting point as high as 2614° C. After consolidation, the CaO mold is very easy to collapse in water or air to form $Ca(OH)_2$ or $CaCO_3$. Thus $CaCO_3$ particulate material is one of the molding/pressure-transmitting media used in this invention.

Mold Making and Core Making

Molds can be made by any proper hand or machine operations, but molding equipment and techniques currently used in the foundry industry are preferred. In this invention a mold can be made of different particulate material in the facing and backing regions of the mold to readily meet individual requirements and reduce costs.

The cold box process, heat-cured process, or no-bake process is used for core making. Injection molding is another process available for core making, having the advantage of high dimensional accuracies. In some cases, the same material used for making the final article, such as steel, is used for core making in order to achieve the same shrinkage rate.

In some cases, the molds may be burned after mold making to remove volatiles, preferably, in an inert atmosphere or under vacuum. The molds still retain good strength.

Alternative Mold Making

In order to produce prototypes, or conduct small quantity productions, at lower cost and with less lead time, two alternative molding methods are used in this invention. In the first alternative, a selected particulate material such as silica sand is coated with a polymer to form polymer coated free flowing particles, or is blended with a polymer powder to form a dry mix, or is mixed with a liquid polymer to form a wet mix. A mold is produced by laser beam sintering of the polymer, or by other electromagnetic radiation beam curing of the polymer in the wet mix or dry mix of polymer coated particles. This shaped curing is performed using stereolithography (SLA), or selective laser sintering (SLS), or fused deposition modeling (FDM). The beam's movement is controlled by software installed on the respective machine and derived from a Computer Aided Design (CAD) file for an article. The beam sinters or cures the polymer layer by layer and the polymer bonds the particles, forming a three-dimensional mold.

As another alternative, a mold is produced by machining blocks made of particulate material and binder, and then assembling the machined components with a glue. For example, carbon particulates are mixed with an organic binder to form blocks by pressing the mixture into boxes. These blocks are soft and readily machined using ordinary machinery.

Coating

In most cases, various coatings are required on internal surfaces of the molds and external surfaces of the cores to prevent reaction between powdered materials and surrounding molding and core making materials. Another purpose is to prevent the penetration of fine powders into the gaps between molding or core making particulates, resulting in particulate and powder sticking.

Five components are the most commonly used for preparing a coating slurry: coating material, carrier system, suspension system, binder system, and chemical modifiers. The coating materials can be carbon, ceramics and refractory metals, including those formed from organic and metallorganic precursors. Binders may be organic or inorganic.

Coatings are applied by spraying, brushing, dipping, or pouring onto internal surfaces of molds, external surfaces of cores, and in some cases directly on pattern surfaces, where they are then bonded. Coatings of multilayered similar materials or multilayered dissimilar materials are also used in this invention.

Articles with functional coatings are also manufactured using this invention in a unique way. There are many applications requiring different surface and bulk properties of an article, produced using coating technologies such as thermal spray coating, plasma spray coating, physical vapor deposition, chemical vapor deposition, bead porous coating, wire porous coating, and so on. Each coating has advantages and disadvantages. Some special applications use metallic, oxide, carbide, nitride, boride, and diamond coatings for improved wear resistance. Others use porous, bioactive material, and calcium phosphate coatings for promoting bone ingrowth, and attachment of surgical implants. In this invention, a slurry, or a paste, or dry particles, or a thin solid or porous preform, containing the desired coating materials are applied or attached to the internal surface of a mold of pressure-transmitting medium and to the outer surface of a core. The desired coating materials include metals, intermetallics, ceramics and carbon (diamond), as single or multiple components (phases). Some of the components may be treated first to have a special distribution of particle sizes or shapes, or coated with a binder or an additive for liquid phase sintering, or blended together to form a composite. Special insulating characteristics may also be achieved. Some of the components may be dissolved or decomposed, or resorbed by a solution, body fluid, moisture, or air, directly or after a heat treatment. Powder fed into the cavity of the mold bonds with the functional coating material at elevated temperature and under high pressure, with the bonding of the functional coating material being strong. The coating may be thin or thick, extensive or localized, single or multicomponent, single or multilayered, or different in different locations. By using multiple layers one may introduce intermediate coatings to coordinate larger property differences between the outer layer and the bulk material, or to produce gradient materials, or to produce gradient porous coating, or to build sufficient thickness. The intermediate coating material may be selected from any metals, intermetallics, ceramics, their mixtures, or chemical compounds, preferably Cu, Ni, Co, Ti, Al, Si, Zr, Mo, V, Cr, Nb, W, Ta, Re, Fe, Mn, Ru, Rh, Y, Mg and their alloys.

In order to reduce potential sticking between the functional coatings and the molding medium, and to increase the bonding between the article and the functional coating, an isolation coating is inserted between the mold and the functional coating. To make a porous coating, one component (phase) of the selected coating material is dissolved or decomposed by a solution or moisture or air, after consolidation. Another coating application is to conduct nitriding, carbonizing, or carbon nitriding, by reaction between the article material and the selected coating material. Typical applications of this coating technique include metal, cermet, ceramic, and intermetallic coating for improvement of wear and corrosion resistances, and CoCrMo on CoCrMo, or Ti on CoCrMo porous coating, or a bioactive ceramic material coating on a metal substrate for improvement of bone and surgical implant attachment.

For example, to manufacture a CoCrMo surgical knee with a porous coating, $CaCO_3$ stone or agglomerates made of CaO powder, a contamination eliminating material, and a binder are crushed and screened to monosize between 50 $\mu$m to 2,000 $\mu$m. An organic binder is applied on the desired surfaces of the mold and the monosized $CaCO_3$ particles are attached to the surfaces by the organic binder. The organic binder is applied on the $CaCO_3$ particles again and second layer of $CaCO_3$ particles are attached to the first layer of $CaCO_3$ particles by the second layer of the organic binder. More layers of binder and $CaCO_3$ particles are applied in the same way until reaching a desired thickness. Fine CoCrMo powder is filled into the mold, and the fine CoCrMo powder slips into the gaps between the $CaCO_3$ particles. After consolidating the powder under a high pressure and an elevated temperature, the $CaCO_3$ particles (one phase) are dissolved by an acid to generate a porous surface.

Another application of this invention is the manufacture of a CoCrMo surgical hip joint with calcium phosphate coating. Calcium phosphate is also called hydroxyapatite (or HA), and is the principal material of human bone. In this example, calcium phosphate powder is mixed with an organic binder to form a slurry. This slurry is applied on the desired surfaces of the mold a few times to form a first HA coating. Calcium phosphate powder is also mixed with an organic binder and dried to form agglomerates. The agglomerates are crushed and screened to form monosized HA particles. An organic binder is applied to the first HA coating and HA particles are attached to the first HA coating by the organic binder. The organic binder is applied to the HA particles again and second layer of HA particles are attached to the first layer of HA particles by the second layer of the organic binder. More layers of binder and HA particles are applied in the same way until a desired thickness is achieved. After filling a fine CoCrMo powder into the mold and consolidation, a CoCrMo surgical hip joint is produced with a fully dense HA coating on its outer surface, and a composite coating consisting of HA particles and CoCrMo material as the inner layer of coating.

A preform produced by other shaping processes can be coated according to the present process as well. A slurry or a paste with coating material and an organic binder is applied to the preform. A mixture of particulate and binder surrounds the preform and cures. Hot isostatic pressure is applied, and the particulate coating adheres to the preform.

Implanting and Mold Assembly

Before assembling a multi-part mold to form an integrated mold, cores and other implants, if any, are inserted and positioned in the molds. The partial molds are then assembled and the assembly is placed in a container. Implants may include any solid or powdered metal, intermetallics, graphite or ceramic pieces for surface finish or dimensional control. Other implants include metal, intermetallics, cermet, or ceramic preforms for diffusion bonding, manufacturing hybrid material articles, and producing porous coating. Also fiber preforms for manufacturing fiber reinforced composite articles are possible.

The function of the container is to exclude air, and to isolate the mold from external contaminants. It also seals out a gas or liquid that may be used to apply consolidation forces. For consolidations at lower temperatures, metallic materials are used for encapsulation. For consolidations at higher temperatures, ceramic materials are used for encapsulation. If an article is made of a brittle material such as a ceramic, the mold is composed of a graphite particulate, BN particulate, calcium carbonate particulate, or mixtures of these components, which are soft for mechanical removal after consolidation, or easy to collapse by other means.

Powder Preparation and Filling

Theoretically, all types of powders, including whiskers and fibers, currently used for producing P/M metallic, intermetallic, ceramic, and composite articles are suitable for use in the present invention. A powder, or mixture of powders, can also be selected to synthesize special materials by an in-mold sintering reaction between powder particles using a controlled atmosphere. This takes place during an initial heating process. For example, 64 wt % titanium powder and 36 wt % aluminum powders can be mixed and filled into a mold. The mold is then heated under vacuum to an elevated temperature. The titanium powder will react with the aluminum powder to form TiAl, an intermetallic material for high temperature applications.

In order to prevent contamination, during heating, of powdered material by harmful gases, such as $O_2$ and $CO_2$ from mold particulates and binder, one or more contamination eliminating materials may be added into the powdered material or mold medium. Contamination eliminating materials include sodium, potassium, yttrium, lithium, beryllium, calcium, scandium, strontium, zirconium, barium, aluminum, titanium, magnesium, manganese, silicon, carbon, copper, zinc, $CaH_2$, and the rare earths. The contamination eliminating material has a higher affinity for the harmful gases than does the powdered material at elevated temperatures. It is preferable to use a contamination eliminating material which forms a harmless gas after reacting with the harmful gases. This harmless gas can then be removed by a vacuum pump. If formation of gaseous by products is impossible, it is preferable to use a contamination eliminating material with a melting point higher than the consolidation temperature. The particle size of the contamination eliminating material should be very fine (finer than 1 mm) to increase the surface area for reaction. The products of the reaction between the contamination eliminating material and the harmful gas, if not gaseous, will remain in the article as a reinforcement or inclusion. Such inclusions may have little negative, or even positive, effect on the article's mechanical properties. The amount of contamination eliminating material to be added is estimated according to the amount of gases released, and the reaction equilibria. It is preferable to use one of the elements in the composition of the article as the contamination eliminating material. Final composition of the article should be met as closely as possible.

Non-monosized powders and multi-phase powders, such as powders with whiskers for reinforcement, should be completely mixed before loading, using an appropriate mixing facility. Appropriate mixers include a ball mill, an attrition mill, or a Turbula mixer as manufactured by Willy A Bachofen AG in Switzerland. Metallic, intermetallic and ceramic powders, or their mixtures, may also be mixed with liquids for wet feeding if the powdered material is of poor dry flowability. A homogeneous mixture of more than one phase is often critical. A liquid may include other additives, such as viscosity modifiers, binders, plasticizers, coupling agents, deflocculants, coagulants, foaming agents, antifoaming agents, and lubricants. The liquid used may be water, mineral oils, vegetable oils or organic solutions such as kerosene, gasoline, or alcohol. The Theological properties of a slurry are important characteristics. It is the intention of this invention obtain a high loading of solid particulates with low viscosity. The purpose of adding a binder, plasticizer and coupling agent is to provide strength and plasticity to overcome the internal stress after the liquid has vaporized. A viscosity modifier may be used to control the viscosity of a slurry and the settling of particulates. Deflocculants and coagulants may be used to control the viscosity, solid loading capability, and packing defects. Foaming and antifoaming agents may be used to eliminate bubbles in a slurry or to form a porous article. A lubricant may be used for improving flowability.

Most ceramic powders are light in weight and fine in size when compared to metal powders. These characteristics make ceramic powders difficult to feed into a mold in dry form, so as to achieve a high packing density. If dry feeding is required for a ceramic powder, then a spray dryer may be used make spherical agglomerates of ceramic powders, which have good flowability and a dense packing structure within the agglomerates.

If dry powders are used, the powders are poured or blown into a cavity through one or several sprues depending on the structure of the mold cavity. A mechanical vibrator and/or manual tapping is used to assist the flow of powders and increase the packing density. If wet feeding is used, the powder paste or slurry is charged via a pressure injection device or machine. The powders are injected under pressure into a cavity through a gate. Air in the cavity is forced out through one or several venting holes. The gate position, shape, and dimensions are carefully designed for a particular application. The injection pressure, injection rate, velocity, holding pressure, and time are controlled in order to obtain the best result.

Initial Reaction Heating and Contamination Elimination

After powder filling, the mold is heated to an elevated temperature in a vacuum or a controlled atmosphere. This procedure may burn the binder and eliminate contaminating gases, or transform the powdered material partially or entirely to another material through high temperature reactions with modifying reactants. Factors that are significant in designing the heating procedure include the powdered material, contamination eliminating material, modifying reactant, molding/pressure-transmitting material, binder, coating material, mold size, and desired transformation of powdered material. The reaction heating and contamination eliminating temperature may range from as low as 300° C. up to 2000° C. The heating rate may be as slow as 0.1° C. per minute, and the dwell time may be as long as several days. The controlled atmosphere may be a vacuum as high as $1 \times 10^{-10}$ torr, or hydrogen, or carbon monoxide, or nitrogen, or argon, or helium, or carbon dioxide, or oxygen, or a mixture of gases. This atmosphere may supply the modifying reactant.

For example, Ti-6Al-4V powder is very reactive with the oxygen released from the particulates and binder which form the mold. In order to produce a Ti-6Al-4V article with oxygen content less than 0.2 wt %, a combination of argon purge and evacuation by a mechanical pump, and a diffusion pump or a turbo pump. This maintains the oxygen level below 1 ppm and the vacuum level below $1 \times 10^{-6}$ torr when the mold is heated up to 1000° C.

As another example, nitrogen can increase the tensile strength of CoCrMo alloy. The mold with CoCrMo powder in its cavity is heated up to 1100° C. and held at that level for a few hours under a vacuum. A gas containing 1% nitrogen and 99% argon is then introduced into the mold. The nitrogen reacts with the CoCrMo powder to increase the nitrogen content of the powder, resulting in higher strength in the final CoCrMo article.

As another example, a mixture of FeO and carbon powders are charged into a mold. The mold is heated up to 1000° C. in a hydrogen atmosphere and then in a vacuum. The FeO powder is reduced to form iron powder by the combination of hydrogen and carbon powder. The iron powder reacts with the carbon powder, forming a carbon steel powder. After consolidation, a carbon steel article is produced.

As yet another example, a mixture of $Al_2O_3$ and silicon powders are charged into a mold. The mold is heated up to 1450° C. in a CO atmosphere. The silicon powder reacts with the CO to form in-situ SiC whiskers. After consolidation, an article of a SiC-whisker-reinforced $Al_2O_3$ composite is produced.

Evacuation and Sealing

After the initial reaction heating of the mold, the container, filled with the mold and powder, is closed, evacuated, and sealed. Closing includes placing a cover on the container and fastening the cover in place using mechanical fasteners, or by crimping, gluing, or welding. This entire process may take place in an evacuated environment. Alternately, the closing may be done in ambient air, followed by evacuation through a stem, which is then sealed by crimping.

Consolidation

The sealed container, with the mold of pressure-transmitting medium and the powdered material inside, is consolidated by hot isostatic pressing (HIP) equipment, or by a pressure sintering furnace using a gas to transmit pressure, or by rapid omnidirectional compaction equipment using a liquid to transmit pressure. The temperature can be as high as 1800° C. and the pressure can be as high as 1 GPa.

Post Treatment

After consolidation, the container is opened by cutting, breaking, or other appropriate means, depending on the container's material.

If an article is made of ductile material such as metal or metal alloys, the separation of an article from the mold is carried out by core knockout, shot blasting, or shakeout equipment.

Combustible mold materials may also be used. For example, a graphite mold may be burned in air to such a degree as to lose strength. A calcium oxide mold may be collapsed in water or in air through reaction with water or water vapor, and carbon dioxide.

To produce a porous coating, as described above, the coated article is etched with an acid, or immersed in water, or exposed to moisture to remove one phase of the coating (e.g. CaO particles derived from the $CaCO_3$ particles). The pores are interconnected. Pore size, shape, volume percentage, and depth are controlled by controlling the size, shape, volume percentage and thickness of the phase ($CaCO_3$ particles) to be removed.

What is claimed is:

1. An article manufactured by a method comprising the steps of:

mixing a particulate material with a binder to form a mold material;

shaping said mold material into a plurality of partial molds having an external surface and an interior cavity and being of sufficient solidity to maintain a shape, yet being compressible under pressure;

assembling said partial molds to form an integrated mold with an interior cavity;

filling said interior cavity with a powdered material to be consolidated;

placing said mold and powdered material in a container;

initially heating said mold to an elevated temperature to remove or fix undesirable gases, or to transform said powdered material partially or entirely to another material;

hermetically sealing the container under vacuum;

subsequently heating said container with said mold and said powdered material to an elevated temperature;

applying pressure to the external surface of said container sufficient to compress said container and said mold, and transfer a pressurizing force to said powdered material within said mold cavity, so as to consolidate said powdered material in said mold cavity and form an article; and removing material surrounding said article from said mold.

2. An article as defined in claim 1, wherein said article is made of metallic, intermetallic, ceramic, or composite materials.

3. An article as defined in claim 1, wherein said article has a hybrid structure.

4. An article as defined in claim 1, wherein said article has a coating.

5. An article as defined in claim 4, wherein said coating comprises metallic, intermetallic, ceramic, diamond, or composite materials.

6. An article as defined in claim 5, wherein said coating comprises porous coating.

7. An article as defined in claim 6, wherein said porous coating comprises CoCrMo on CoCrMo porous coating.

8. An article as defined in claim 6, wherein said porous coating comprises a Ti or Ti alloy on CoCrMo substrate porous coating.

9. An article as defined in claim 5, wherein said coating comprises a calcium phosphate coating.

* * * * *